(12) United States Patent
Cordeiro et al.

(10) Patent No.: US 8,303,546 B2
(45) Date of Patent: Nov. 6, 2012

(54) LOCKING DEVICE FOR ENDOLUMINAL PROSTHESIS DELIVERY SYSTEM

(75) Inventors: Eduardo Jose Cordeiro, University Heights, OH (US); Luciano Almeida Fleury Curado, Goias (BR); Luana Beatriz Pertile Dezanet, Goias (BR)

(73) Assignee: Scitech Produtos Medicos Ltda, Goias (BR)

( * ) Notice: Subject to any disclaimer, the term of this patent is extended or adjusted under 35 U.S.C. 154(b) by 493 days.

(21) Appl. No.: 12/565,421

(22) Filed: Sep. 23, 2009

(65) Prior Publication Data

US 2010/0094393 A1   Apr. 15, 2010

(51) Int. Cl.
*A61M 5/32* (2006.01)
(52) U.S. Cl. .................................... 604/178; 604/250
(58) Field of Classification Search .................. None
See application file for complete search history.

(56) References Cited

U.S. PATENT DOCUMENTS

| 6,575,932 B1 * | 6/2003 | O'Brien et al. | 604/101.01 |
| 7,104,982 B2 * | 9/2006 | McDaniel | 604/533 |

* cited by examiner

*Primary Examiner* — Thomas J Sweet
*Assistant Examiner* — Christopher D Prone
(74) *Attorney, Agent, or Firm* — Tarolli, Sundheim, Covell & Tuummino LLP

(57) ABSTRACT

A locking device for preventing movement of an elongated instrument includes a tubular base that has an outer surface and an inner surface. At least one lateral opening extends through the tubular base from the outer surface through the inner surface. At least one rocker arm is mounted to the base. Each of the rocker arms has a locking projection that extends radially inwardly aligned with one of the lateral openings of the base. An actuating member is rotatable relative to the base portion between first and second positions. In the first position the actuating member engages the rocker arm to urge the locking projection radially inward through the lateral opening and beyond the inner surface of the tubular base. Movement of the actuating member to the second position causes the locking projection to move radially outward through at least a portion of the lateral opening.

23 Claims, 10 Drawing Sheets

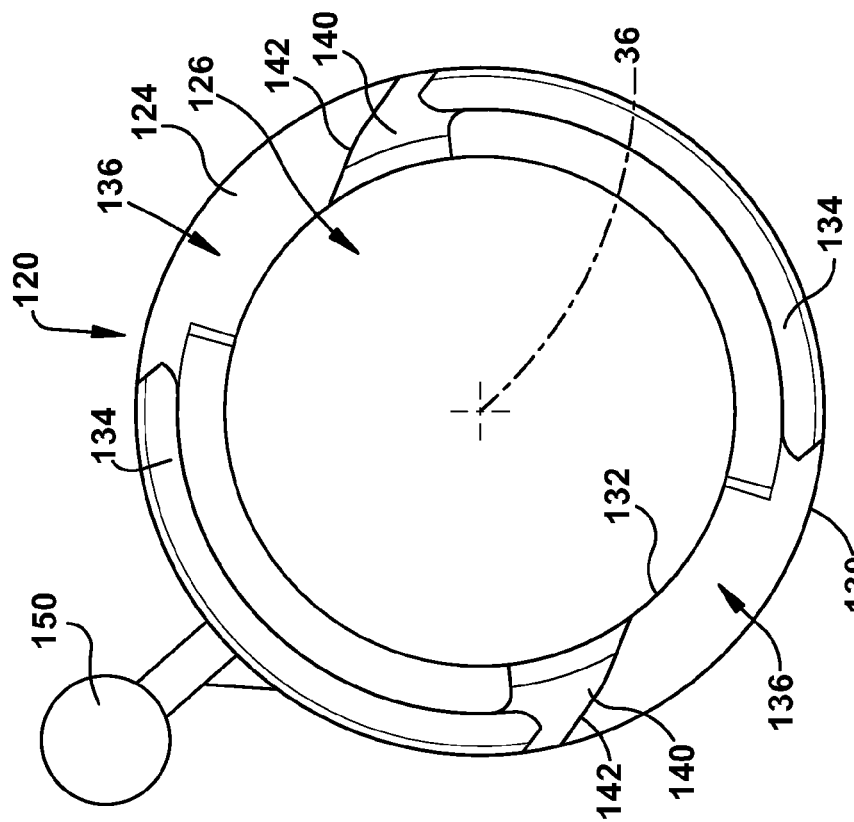
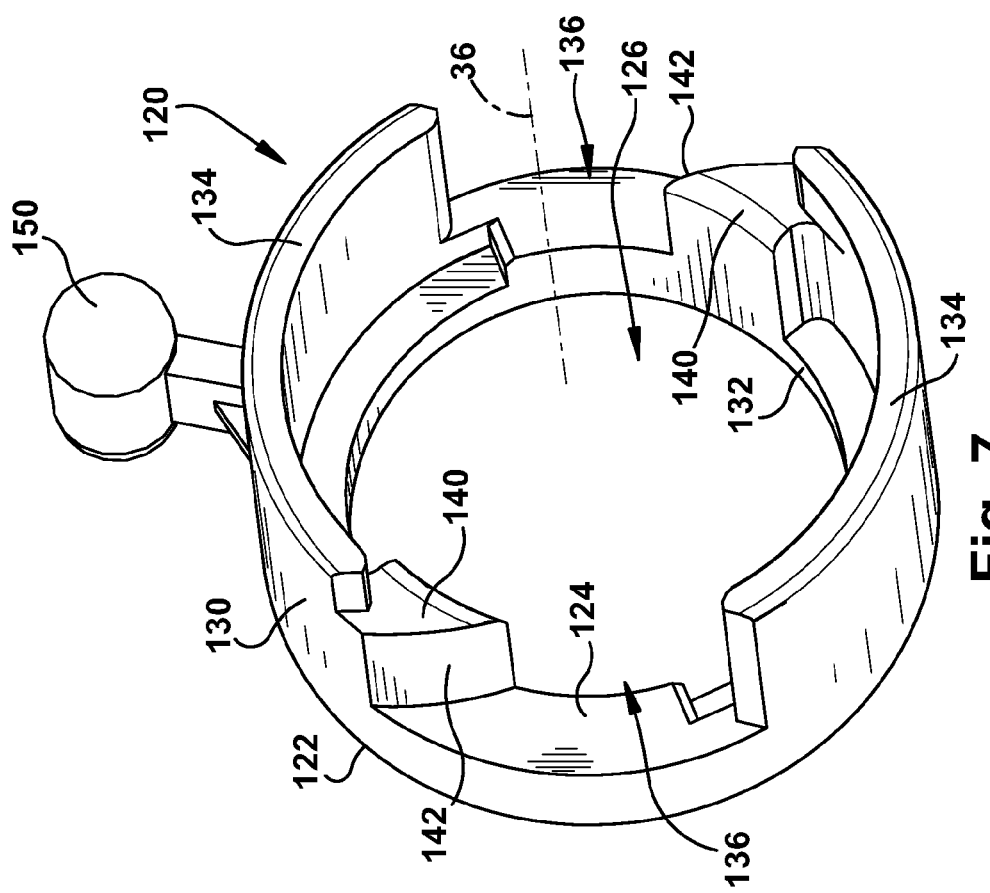

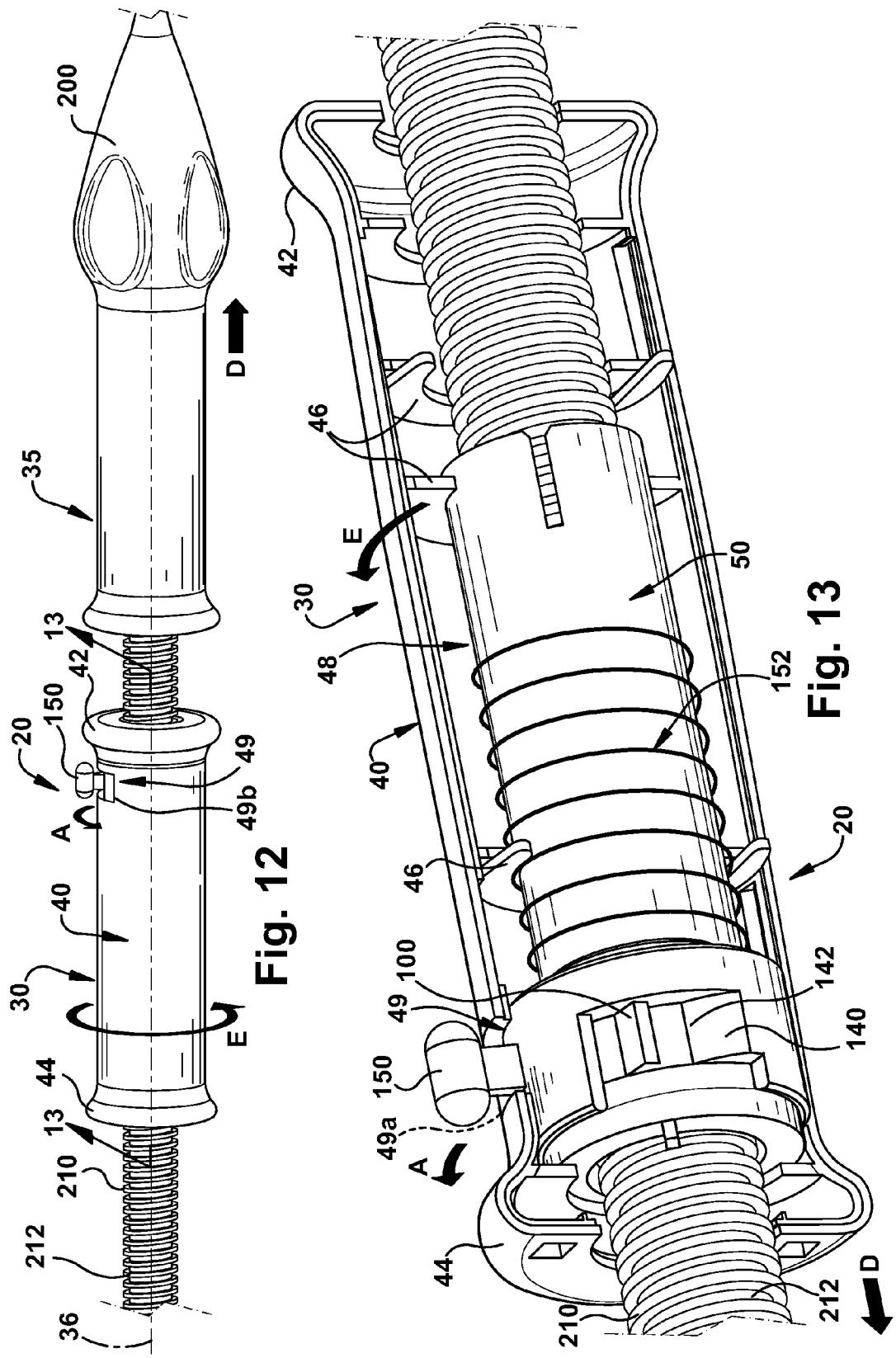

LOCKING DEVICE FOR ENDOLUMINAL PROSTHESIS DELIVERY SYSTEM

RELATED APPLICATION

This application claims priority under 35 U.S.C. §119 to Brazilian Patent Application No. MU 8802275-7, filed Oct. 13, 2008, the entirety of which is incorporated herein by reference.

TECHNICAL FIELD

The invention relates to a locking device and in particular to a locking device for delivering medical instruments.

BACKGROUND

Endoluminal prostheses are commonly used in the medical field to treat disease such as obstructive diseases, non-obstructive diseases, and degenerative diseases. The endoluminal prosthesis is frequently deployed under fluoroscopic guidance or other imaging system in order to position the prosthesis in the desired anatomical site. For example, the endoluminal prosthesis may be deployed within the vasculature of a patient to treat an obstructed vessel.

More specifically, endoluminal prostheses may be used in the minimally invasive endovascular repair of vascular diseases, such as arteriosclerosis and abdominal and thoracic aortic aneurysms. For example, the endovascular procedure requires two small incisions in the groin. Under fluoroscopic guidance, the delivery system containing a vascular prosthesis is guided along the artery from the groin to inside the aneurysm where the prosthesis is released and remains positioned.

In some cases, due to the tortuosity and calcification of the iliac and femoral arteries, increased strength is required to release the prosthesis. In conventional delivery systems, the release is made by relative movement between two handlers: one fixed handler and another handler mobile depending on the configuration of the device. Generally, the prosthesis is released through movement of the distal handler. These delivery systems, however, use linear free movement of the prosthesis without any locking mechanism and/or fine adjustment control of the prosthesis positioning. Furthermore, the current delivery systems require high forces to release the prosthesis, thereby reducing the precision of the delivery position.

BRIEF DESCRIPTION OF THE DRAWINGS

FIG. 7 is a perspective view of an actuating member of the locking device of FIG. 1.

FIG. 8 is a front view of the actuating member of FIG. 7.

FIG. 12 is a perspective view of the locking device of FIG. 1 in combination with a front handle.

FIG. 13 is a sectional view of the locking device of FIG. 12 taken along lines 13-13.

DETAILED DESCRIPTION

Figure 1:
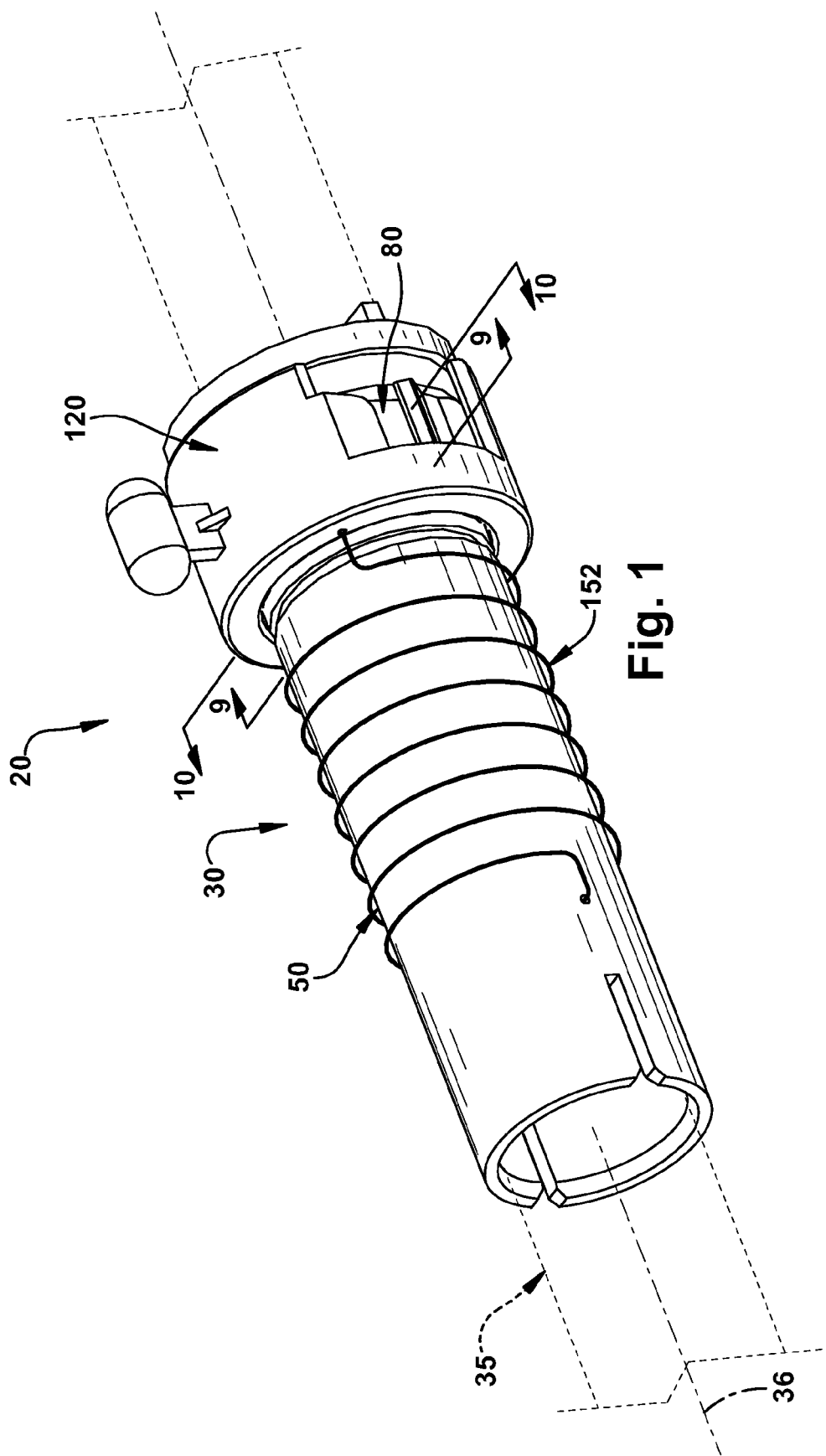
FIG. 1 is a schematic illustration of a locking device in accordance with the present invention.
Figure 2:
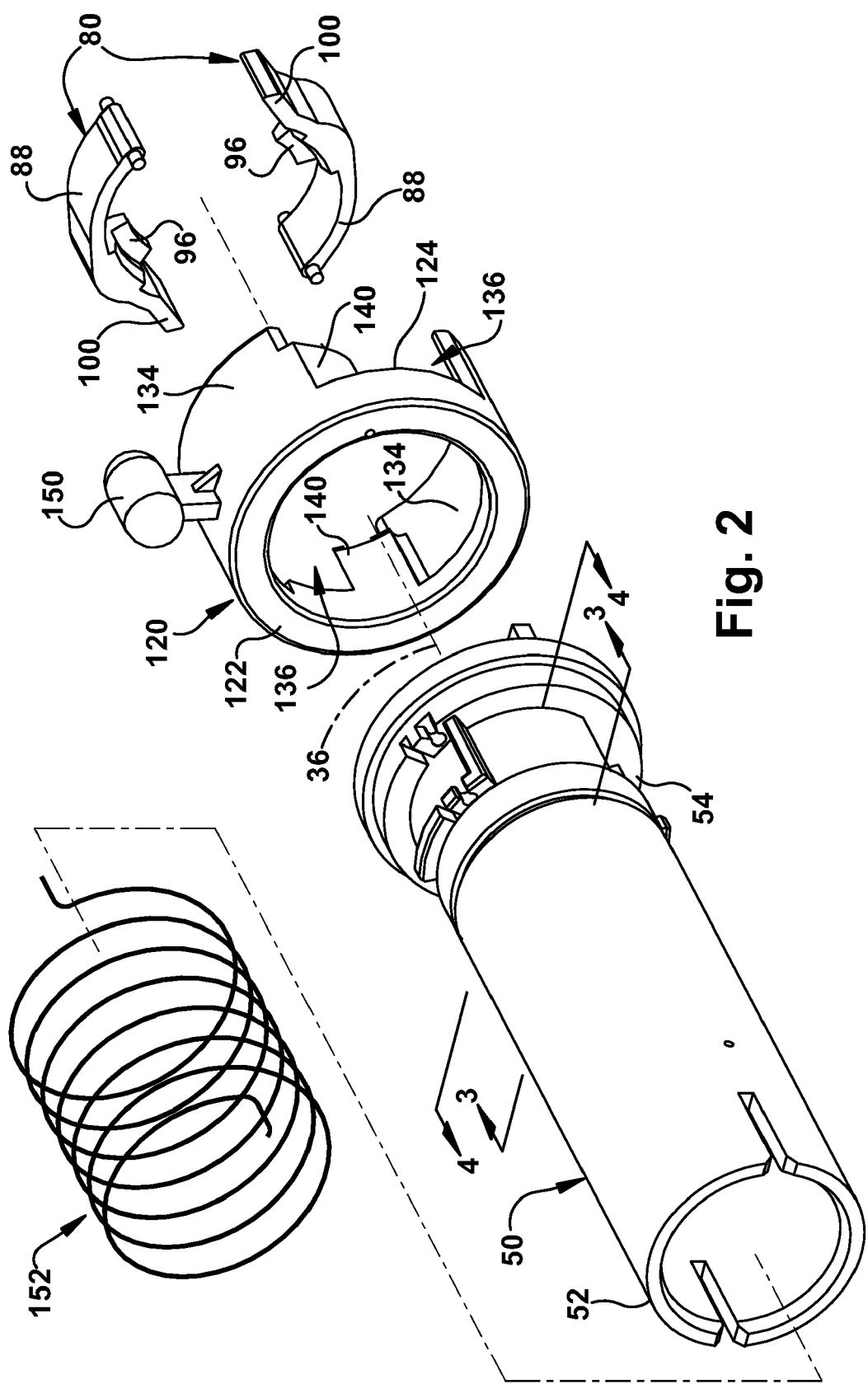
FIG. 2 is an exploded view of the locking device of FIG. 1.

The invention relates to a locking device and in particular to a tangential locking device for delivering medical instruments. A locking device 30 in accordance with the present invention is illustrated in FIGS. 1-2. The locking device 30 is mounted about an elongated instrument, illustrated schematically as 35. The elongated instrument 35 may constitute any instrument, such as a medical instrument for use in medical procedures. For example, the elongated instrument 35 may constitute a stent, a catheter, guidewire, cannula or the like. The elongated instrument 35 may have a smooth outer surface or may be provided with structure, such as ribs, threads, etc. that mate with corresponding structure on the locking device 30. Regardless of the particular construction of the elongated instrument 35, the locking device 30 regulates axial movement of the elongated instrument along a central longitudinal axis 36 that extends through the elongated instrument and the locking device.

Figure 3:
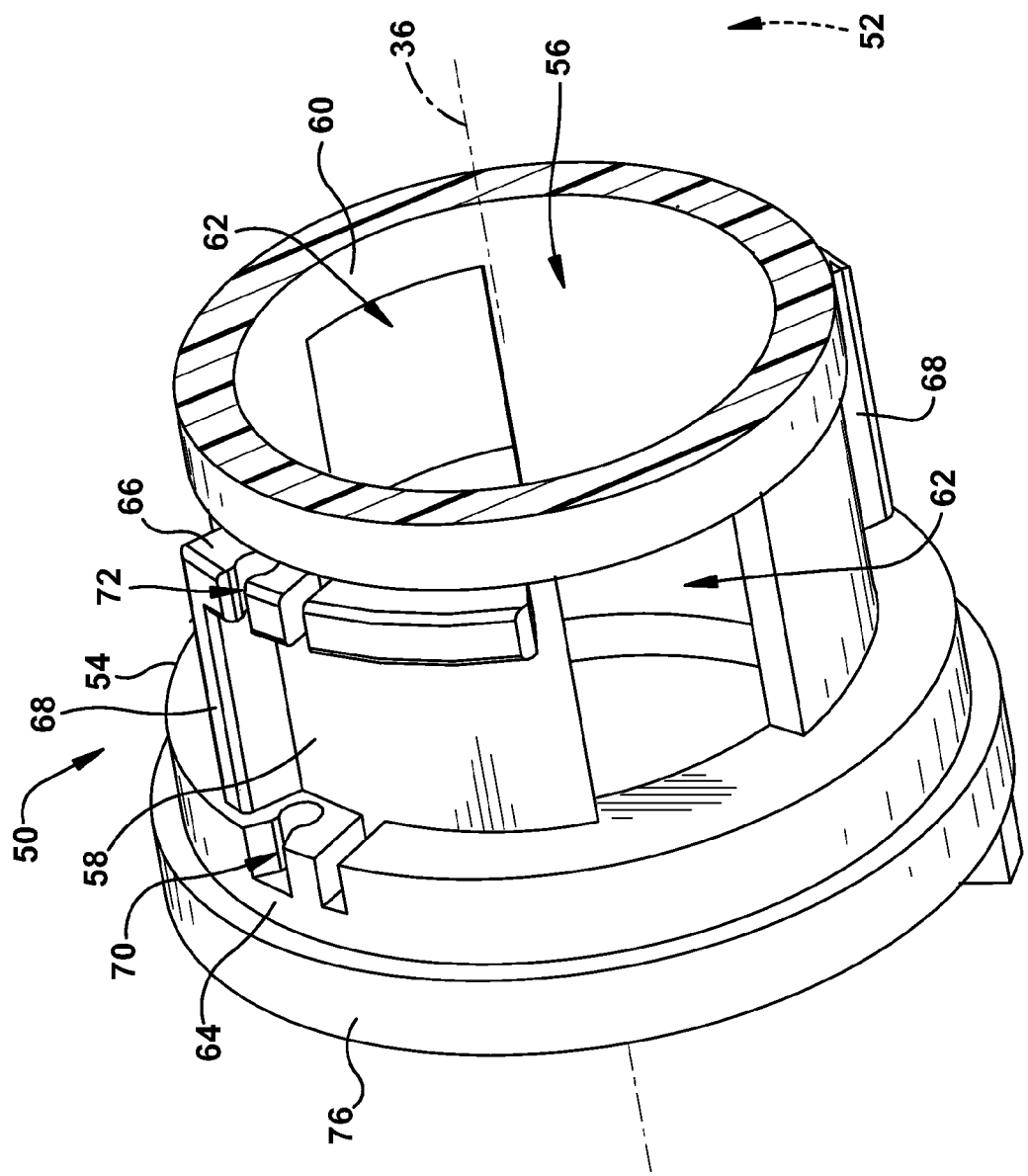
FIG. 3 is a sectional view of a portion of the locking device of FIG. 1 taken along line 3-3.
Figure 4:
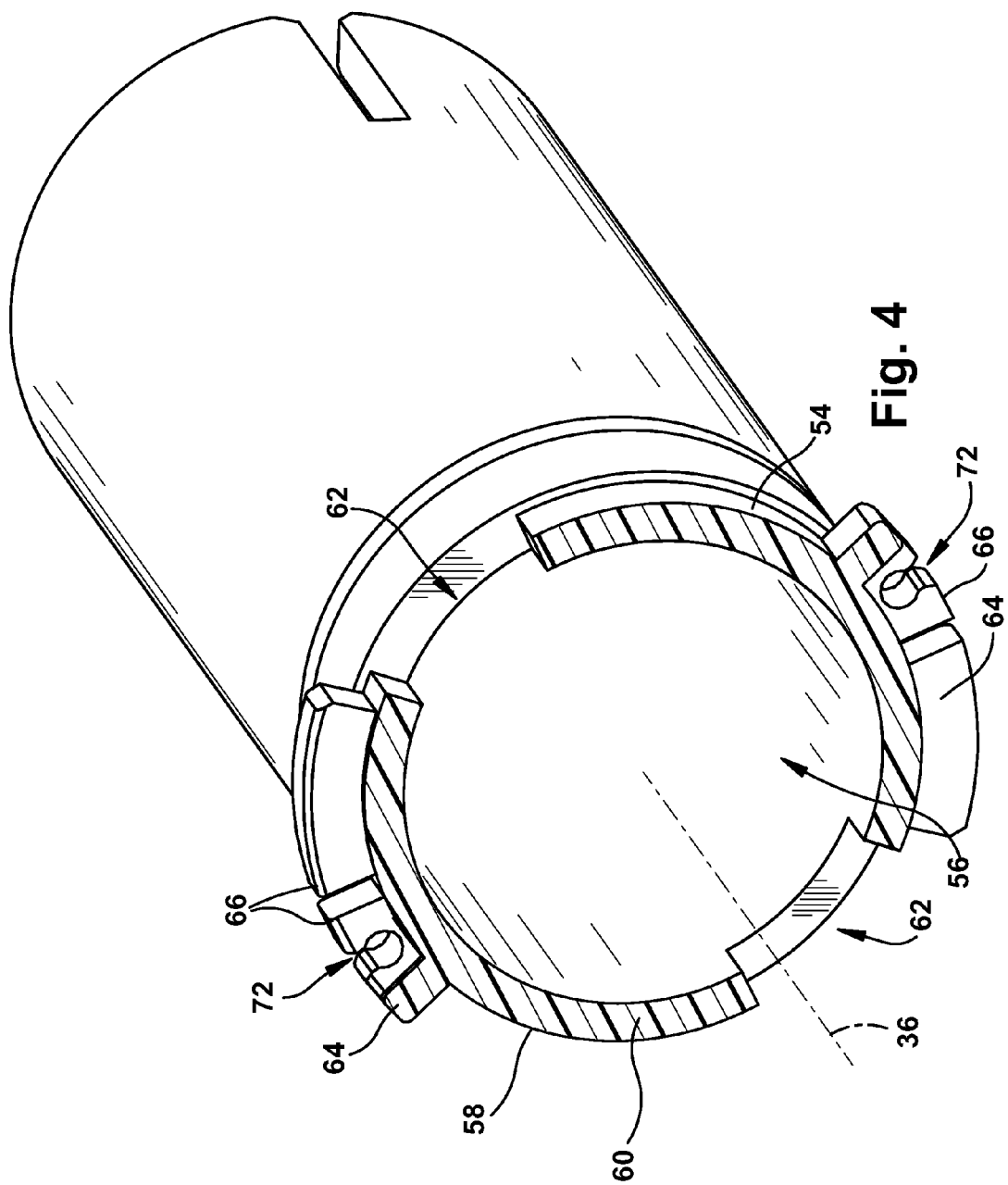
FIG. 4 is a sectional view of a portion of the locking device of FIG. 1 taken along line 4-4.

The locking device 30 includes a base 50, at least one rocker arm 80 coupled to the base, and an actuating member 120. FIGS. 2-4 illustrate that the base 50 has a generally tubular shape. Although the base 50 is illustrated as having a circular cross-sectional shape, those having ordinary skill will appreciate that the base may likewise have another shape, such as triangular, square, rectangular, elliptical or otherwise any polygonal cross-sectional shape. The base 50 may be constructed of any material such as metals, plastics or combinations thereof.

The base 50 extends along the central axis 36 and includes a first end 52 that is spaced axially from a second end 54. An outer surface 58 and a substantially concentric inner surface 60 connect the first end 52 to the second end 54. The inner surface 60 defines a passage 56 for receiving the elongated instrument 35. At least one lateral opening 62 extends from the outer surface 58 through the inner surface 60 at the second end 54 of the base 50. The lateral openings 62 may have any shape, such as rectangular, square, circular or any other polygonal shape. FIG. 3 illustrates two lateral openings 62 diametrically opposed from one another relative to the central axis 36, although those skilled in the art will appreciate that more or fewer openings may be provided and spaced about the base 50 in any configuration.

A series of projections 64 and 66 extends radially outwards from the outer surface 58 around the periphery of the second end 54 of the base 50 and substantially parallel to one another. In particular, a first projection 64 extends circumferentially around a substantial amount or all of the periphery of the second end 54 of the base 50. At least one second projection 66 extends substantially parallel to the first projection 64 and may be positioned closer to or farther from the first end 52 of the base 50 than the first projection. Each second projection 66 is operatively associated with a respective lateral opening 62 in the base 50. As shown in FIG. 3, the second projections 66 are provided adjacent to both of the lateral openings 62. The second projections 66 can be diametrically opposed from one another about the central axis 36. A pair of connecting members 68 extend substantially perpendicular to the first projection 64 and the second projections 66 and connect the first projection to each of the second projections.

The first projection 64 and each of the second projections 66 includes pin receiving recesses 70 and 72, respectively. In particular, the first projection 64 includes a pair of diametrically opposed pin receiving recesses 70 positioned in proximity to each of the lateral openings 62. The pin receiving recess 72 in each of the second projections 66 is aligned axially with one of the pin receiving recesses 70 in the first projection 70. Each pair of pin receiving recesses 70 and 72 is aligned axially and substantially parallel to the central axis 36 of the base 50. Each of the recesses 70 and 72 may constitute a rounded notch extending through a portion or all of the first projection 64 and the second projection 66, respectively. Alternatively, the pin receiving recesses 70 and 72 may have other shapes, such as triangular, square, rectangular or any other polygonal or arcuate shape.

Figure 6:
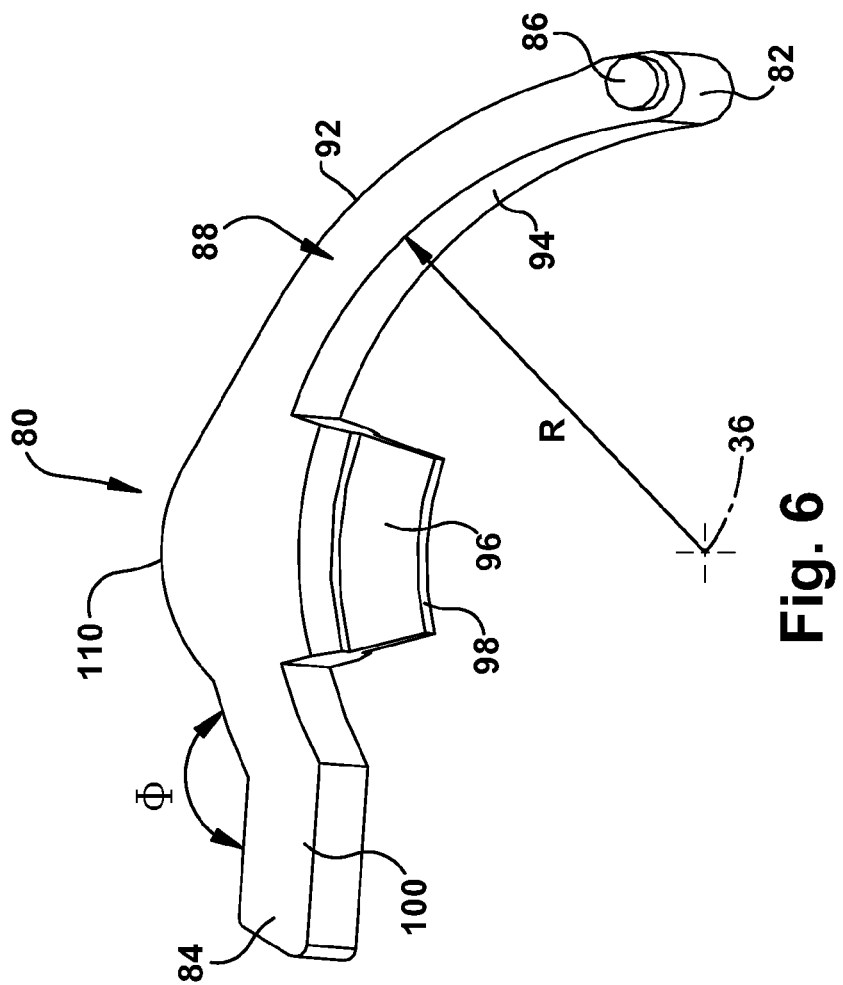
FIG. 6 is a front view of the rocker arm of FIG. 5.
Figure 5:
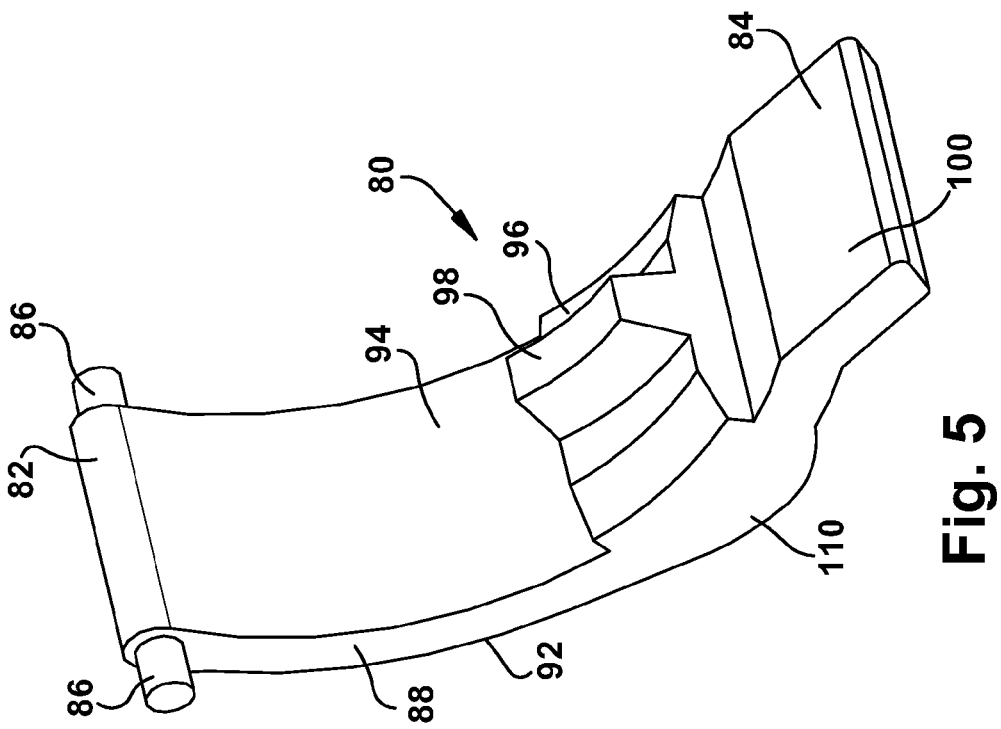
FIG. 5 is a perspective view of a rocker arm of the locking device of FIG. 1.

The base 50 further includes a third projection 76 that extends circumferentially around the entire periphery of the second end 54 of the base 50 and radially outward from the outer surface 58. The third projection 76 may extend radially outward farther than the first projection 64, such as shown in the example of FIG. 3. The first projection 64 is positioned between the second projections 66 and the third projection 76 along the central axis 36. FIGS. 5-6 illustrate an example of one of the rocker arms 80 according to an embodiment of the present invention. The rocker arm 80 has a generally arcuate shape and includes a first end 82 and a second end 84. The rocker arm 80 may be constructed of any material such as metals, plastics or combinations thereof. The first end 82 includes one or more pins 86 that extend outward from the first end. The pins 86 may be circular in shape or may have any polygonal shape so long as the shape of the pins substantially corresponds with the shape of the pin receiving recesses 70 and 72 in the base 50.

The rocker arm 80 includes an arm portion 88 and a cam portion 100 that extends at an angle Φ relative to the arm portion 88. The angle Φ may be acute, perpendicular or obtuse. The arm portion 88 has a radius of curvature, indicated by R, relative to the central axis 36 that substantially corresponds with the curvature of the outer surface 58 of the base 50. The arm portion 88 includes an outer surface 92 and an inner surface 94. A locking projection 96 extends radially inward from the inner surface 94 towards the central axis 36. The locking projection 96 may have any shape, such as triangular, conical, rectangular, frustoconical, pyramid, frustopyramid, etc. so long as the locking projection can fit through at least a portion of the lateral opening 62 in the base 50. The locking projection 96 terminates at a radially inward locking surface 98.

A retaining portion 110 extends radially outward from the outer surface 92 of the arm portion 88 away from the central axis 36. The retaining portion 110 may constitute an enlarged portion of material thickness or otherwise any structure extending radially outward from the outer surface 92 of the arm portion 88.

An example of the actuating member 120 is illustrated in FIGS. 7-8. The actuating member 120 has a tubular shape and extends along the central axis 36. The actuating member 120 may be constructed of any material, such as metals, plastics or combinations thereof. The actuating member 120 includes a first end 122 that is spaced axially from a second end 124. An outer surface 130 and a substantially concentric inner surface 132 connect the first end 122 to the second end 124. The inner surface 132 defines a passage 126 for receiving the base 50 and the at least one rocker arm 80.

At least one arcuate retaining portion 134 extends axially away from the second end 124 towards the first end 122 and in a direction parallel to the central axis 36. The number of retaining portions 134 corresponds with the number of rocker arms 80 and the number of lateral openings 62 in the base 50. Accordingly, although two retaining portions 134 are illustrated, those having ordinary skill will appreciate that more or fewer retaining arms may be provided. The two retaining portions 134 are diametrically opposed from one another about the central axis 36. Each of the retaining portions 134 terminates with a cam portion 140. The cam portion 140 may have a triangular shape or any other polygonal or curved shape configured to engage the cam portion 100 on the rocker arm 80. The cam portion 140 terminates with a leading surface 142.

Lateral openings 136 extend through a sidewall of the actuating member 120. For instance, each lateral opening 136 extends from the leading surface 142 of the cam portion 140 of one of the retaining portions 134 to the trailing edge of the next retaining portion around the periphery of the actuating member 120. The actuating member 120 further includes a handle 150 that extends radially outwardly from the outer surface 130 of the actuating member. The handle 150 can be configured to be grasped or otherwise manipulated by hand.

Figure 9:
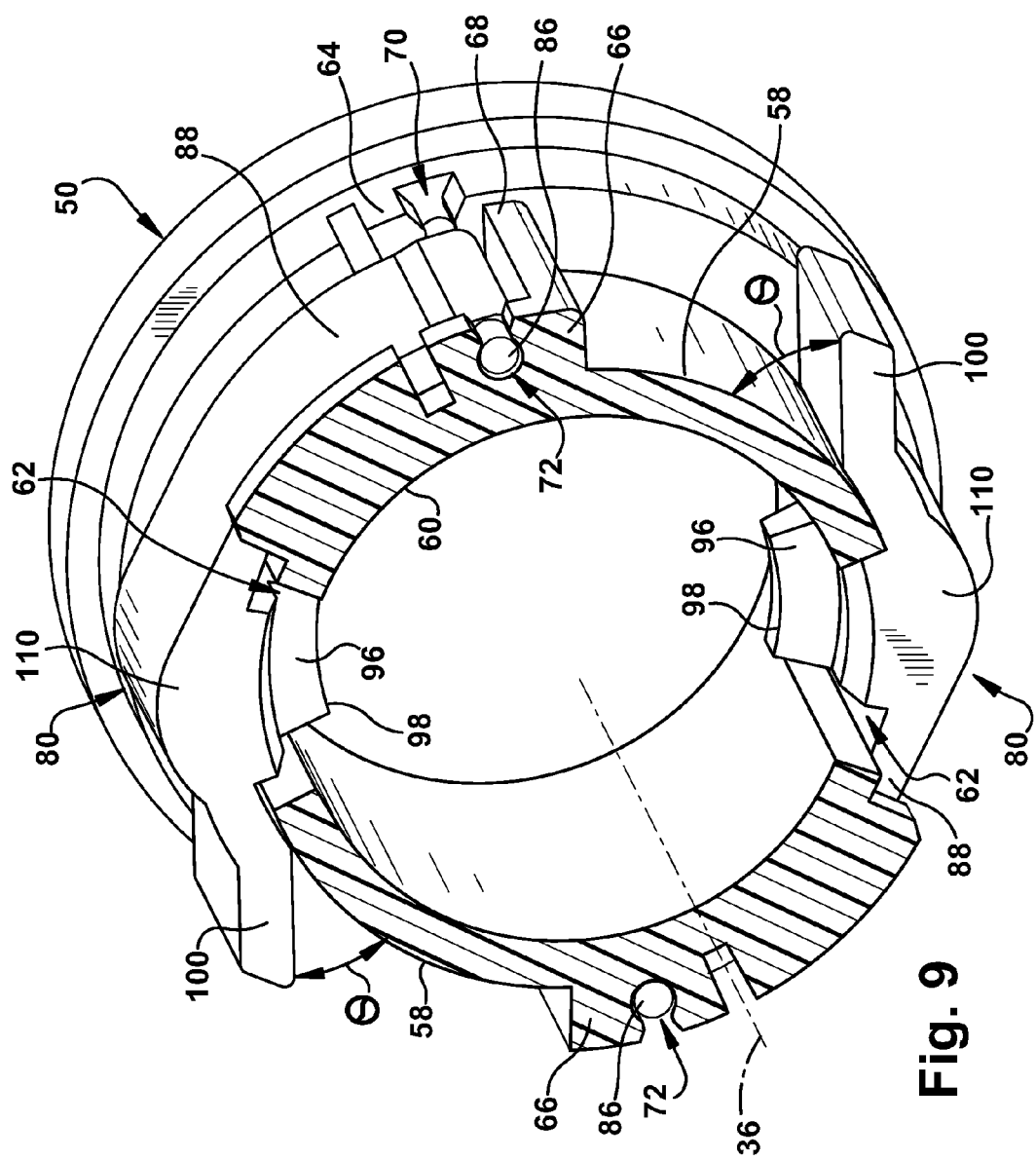
FIG. 9 is a sectional view of the locking device of FIG. 1 in a partially assembled condition taken along line 9-9.

By way of example, to assemble the locking device 30, the rocker arms 80 are mounted to the base 50 as shown in FIG. 9. The pins 86 of each rocker arm 80 are secured within one of the pairs of pin receiving recesses 70 and 72. In other words, the pins 86 of one rocker arm 80 are secured within a pair of pin receiving recesses 70 and 72 on one side of the central axis 36 of the base 50 and pins of the other rocker arm are secured within the pair of pin receiving recesses on the diametrically opposite side of the central axis of the base.

In this configuration, each rocker arm 80 becomes pivotally mounted to the base 50 about the connections between the pins 86 of each arm and the pin receiving recesses 70 and 72. Although a pivotal connection is illustrated, those having ordinary skill will appreciate that the rocker arms 80 could be mounted to the base 50 in alternative ways. For instance, a flexible member/connection could connect the rocker arms 80 to the base 50 or a leaf spring could connect the rocker arms to the base.

As shown in FIG. 9, when the rocker arms 80 are secured to the base 50, the inner surface 94 of the arm portion 88 of each rocker arm 36 overlies and engages upon the outer surface 58 of the base on both sides of the adjacent, corresponding lateral opening 62. In this position, the central axis 36 of the base 50 and the central axis of the rocker arms 80 are substantially co-axial. Also, in this position, the cam portion 100 of each rocker arm 80 extends at an angle θ relative to the outer surface 58 of the base 50.

When the inner surface 94 of the arm portion 88 of each rocker arm 80 overlies the outer surface 58 of the base 50, the locking projection 96 of each rocker arm extends through the corresponding lateral opening 62 such that the locking surface 98 is positioned radially inward of the inner surface 60 of the base. Since the rocker arms 80 are pivotable about the pins 86, the rocker arms can be pivoted or otherwise moved radially outward relative to the base 50 such that the locking projection 96 on each rocker arm is radially moveable through at least a portion of the corresponding lateral opening 62. A spring (not shown) may bias each of the rocker arms 80 and, thus, the locking projections 96 of the rocker arms radially outward relative to the central axis 36 of the base 50.

Figure 10:
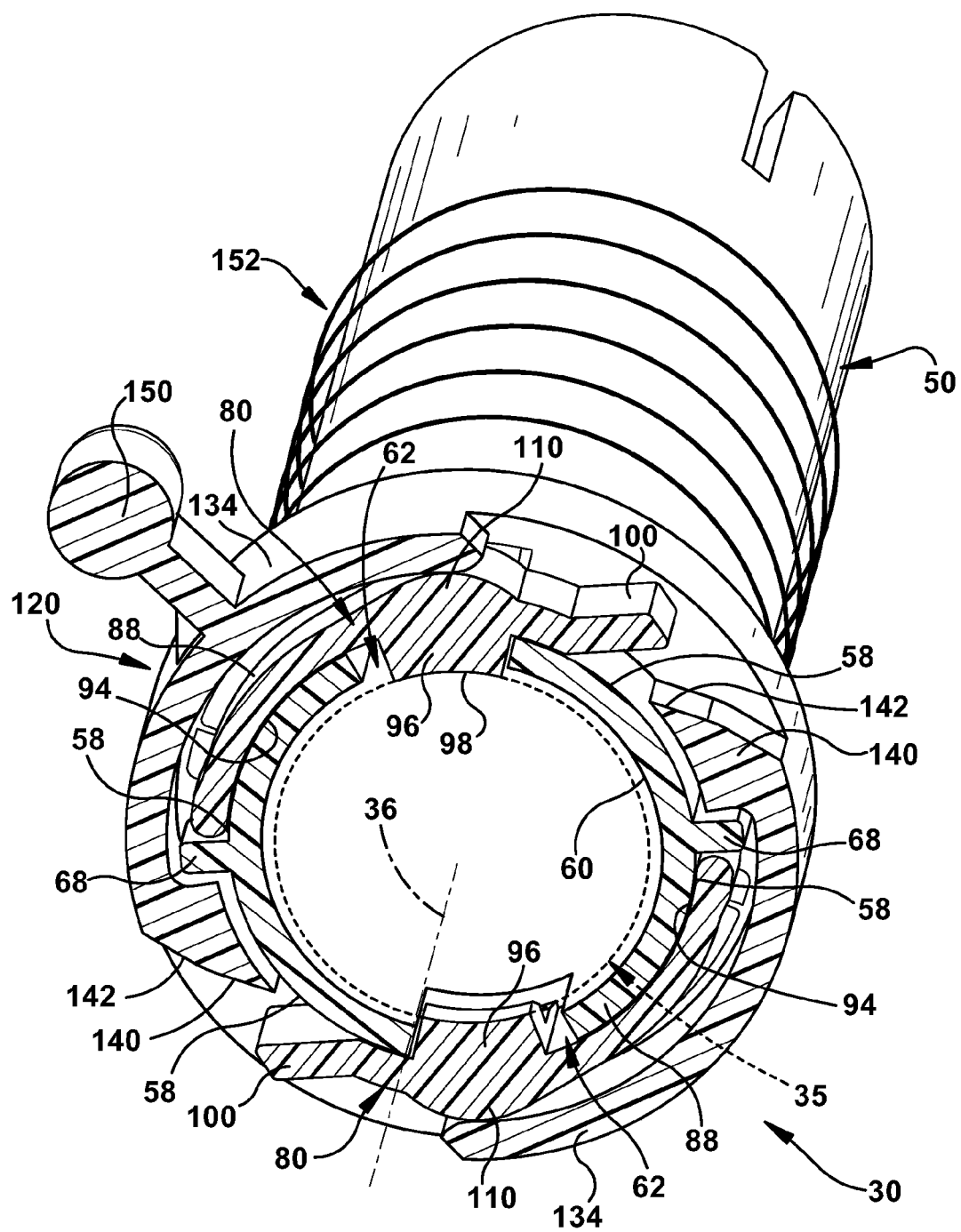
FIG. 10 is a sectional view of the locking device taken along line 10-10 in FIG. 1 with the locking device in a locked position.

Once the rocker arms 80 are connected to the base 50, the base can be inserted into the central passage 126 of the actuating member 120. For instance, the base 50 can be inserted into the actuating member 120 until the second end 124 of the actuating member abuts the third projection 76 on the base to prevent further axial movement of the actuating member relative to the base. The actuating member 120, however, remains rotatable about the axis 36 relative to the base 50. When the actuating member 120 is mounted over the base 50, the actuating member overlies the rocker arms 80 as shown in FIG. 10 (see also FIGS. 1-2). The central axes 36 of the base 50, the rocker arms 80, and the actuating member 120, respectively, are co-axial when the actuating member is mounted over the base.

The actuating member 120 is radially oriented about the base 50 such that each retaining portion 134 of the actuating member initially engages one of the rocker arms 80. More specifically, each actuating portion 134 engages the retaining portion 110 of a rocker arm 80 to urge the rocker arm and, thus, the locking projection 96 of the rocker arm radially inward through the lateral opening 62 and beyond the inner surface 60 of the base 50. Since the rocker arm 60 is urged radially inward when the actuating member 120 is in a first or locked position, the rocker arm is prevented from pivoting or otherwise moving radially outward relative to the central axis 36 of the base 50.

A spring 152 connects the actuating member 120 relative to the base 50 for biasing the actuating member into the locked position, i.e., in a clockwise direction as viewed in FIG. 10. Clockwise rotation of the actuating member 120 is limited by the contact between the cam portion 140 and the connection members 68 on the base 50. For example, the spring 152 biases the actuating member 120 in a clockwise direction until the cam portions 140 on the actuating member abut the connecting members 68 on the base 50. The connecting members 68 therefore act as stops to limit rotational movement of the actuating member 120 relative to the base 50.

The locking projections 96 and the elongated instrument 35 are configured such that, when the actuating member 120 is in the locked position (see FIG. 10), the locking surfaces 98 on the projection 96 extend radially inward beyond the surface 60 of the base 50, and thus can engage the elongated instrument to prevent the elongated instrument from substantially moving axially relative to the base 50. If the elongated instrument 35 has a smooth outer surface, the locking surfaces 58 may frictionally engage the outer surface. Alternatively, the elongated instrument 35 may have a threaded outer surface or may otherwise have structure, e.g., ribs, projections, recesses, etc., into which the locking surfaces 98 of the locking projections 96 can extend.

When the actuating member 120 is in the locked position, the cam portions 100 of each rocker arm 80 extend through a corresponding lateral opening 136 in the actuating member. In other words, the cam portion 100 of each rocker arm 80 extends between the retaining portions 134 of the actuating member 120. In this locked configuration, the cam portions 140 of the actuating member 120 and, thus, the leading surfaces 142 of the cam portions are spaced from the cam portions 100 of the rocker arms 80.

Figure 11:
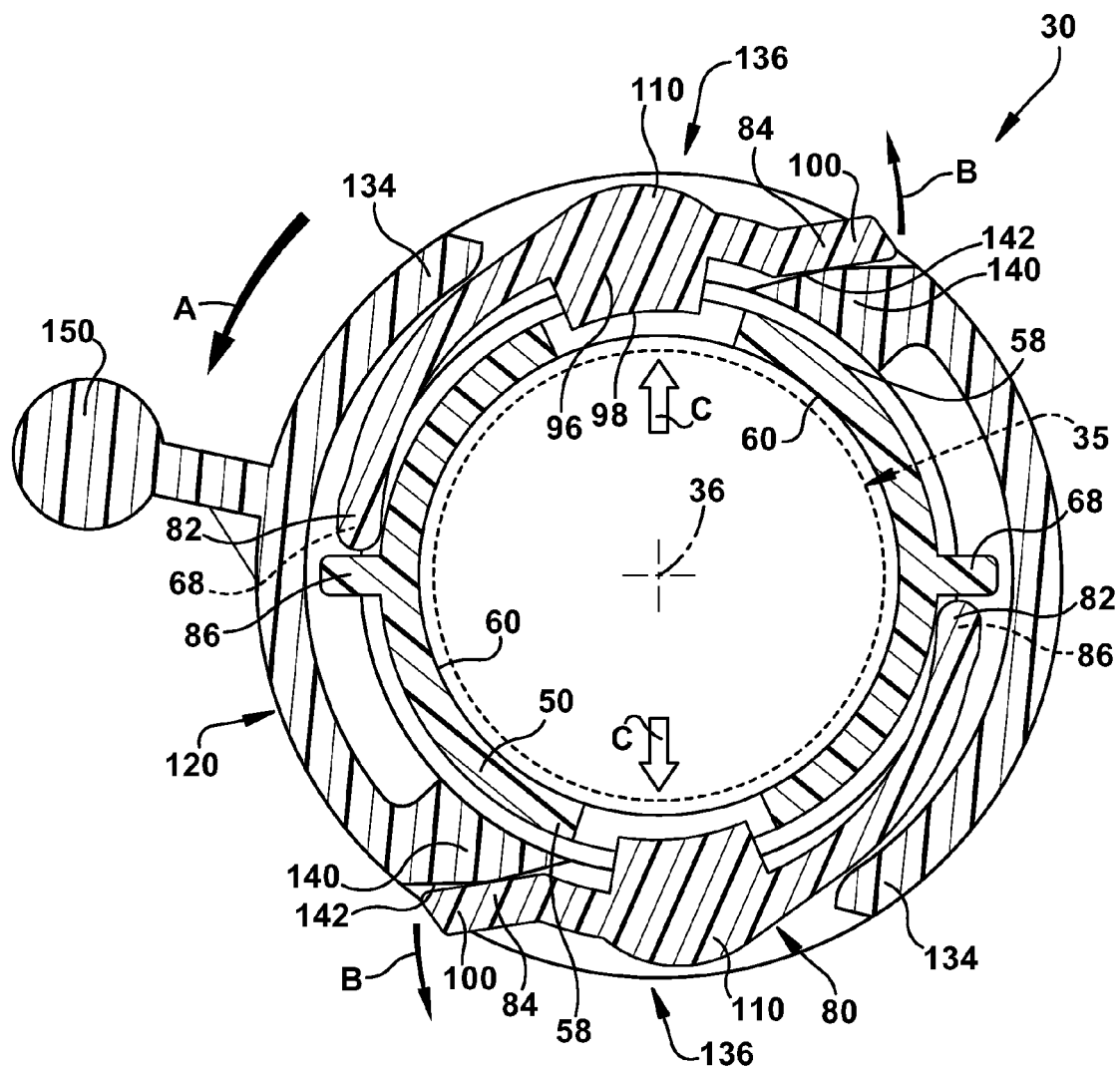
FIG. 11 is a front view of the locking device of FIG. 10 with the locking device in an unlocked position.

As described herein, the actuating member 120 is rotatable relative to the base 50 about the central axis 36 when the actuating member is mounted to the base. The actuating member 120 is therefore rotatable from the first, locked position (FIG. 10) to a second, unlocked position as shown in FIG. 11. To rotate the actuating member 120 to the unlocked position, the handle 150 on the actuating member is grasped or otherwise manipulated in the direction indicated by arrow A. Since the rocker arms 80 are connected to the base 50 and the actuating member 120 is not rigidly mounted to the base, rotation of the handle 150 and associated actuating member in the direction A causes the actuating member to rotate relative to the base and the rocker arms. Furthermore, since the spring 152 biases the actuating member 120 in a direction opposite of direction A, rotation of the actuating member towards the unlocked position is against the bias of the spring. Accordingly, to move the actuating member 120 towards the unlocked position sufficient force must be applied to move the handle 150 in the direction A.

When the actuating member 120 is rotated in the direction A to the unlocked position (FIG. 11), the retaining portions 134 of the actuating member are moved out of engagement with the retaining portions 110 of the rocker arms 80. That is, in the unlocked position of FIG. 11, the retaining portions 134 of the actuating member 120 no longer urge the locking projections 96 radially inward through the lateral openings 62 and beyond the inner surface 60 of the base 50.

As the retaining portions 134 of the actuating member 120 move out of engagement with the retaining portions 110 of the rocker arms 80, the cam portions 140 of the actuating member move away from the connection members 68 on the base 50 and into engagement with the cam portions 100 of the rocker arms. For instance, as the handle 150 rotates the actuating member 120 in the direction A towards the unlocked position, the leading surfaces 142 of the cam portions 140 move counterclockwise (as viewed in FIG. 11) into engagement with the cam portions 100 of the rocker arms 80. The engagement between the cam portions 140 of the actuating member 120 and the cam portions 100 of the rocker arms 80 is facilitated by the angulation θ between the cam portions 100 and the outer surface 58 of the base 50 (see FIG. 9).

Further movement of the actuating member 120 towards the unlocked position causes the leading surfaces 142 of the cam portions 140 to urge the cam portions 100 of the rocker arms 80 radially outward relative to the outer surface 58 of the base 50. Since the first ends 82 of the rocker arms 80 are pivotally connected to the base 50 by the pins 86, urging the cam portions 100 and, thus, the seconds ends 84 of the rocker arms radially outward relative to the outer surface 58 of the base 50 causes the rocker arms to pivot about the pins 86 as indicated by arrow B. The rocker arms 80 are capable of rotating radially outward from the outer surface 58 of the base 50 because the retaining portions 134 of the actuating member 120 have been rotated out of engagement with the retaining portions 110 of the rocker arms. In other words, when the actuating member 120 is rotated to the unlocked position the lateral openings 136 in the actuating member move into radial alignment with the retaining portions 110 of the rocker arms 80. The rocker arms 80 are therefore capable of moving radially outward relative to the outer surface 58 of the base 50 and through at least a portion of the corresponding lateral openings 136 in the actuating member 120.

When the rocker arms 80 pivot in the direction B, the cam portions 100 move radially outward through at least a portion of the lateral openings 136 in the actuating member 120. As a result, the locking projections 96 (being part of the rocker arms 80) move radially outward through at least a portion of the lateral openings 62 in the base 50 as indicated by arrow C.

An example of a delivery system 20 using the locking device 30 of the present invention is illustrated in FIGS. 12-13. The delivery system 20 includes a generally tubular cover 40 that has a first end 42 and a second end 44. The cover 40 may be constructed of any rigid material such as metals, plastics or combinations thereof. A passage 48 extends from the first end 42 to the second 44 and is configured to receive the assembled locking device 30. The cover 40 further includes a plurality of support members 46 that support the locking device 30 within the passage 48.

When the assembled locking device 30 is positioned within the cover 40, the handle 150 on the actuating member 120 extends through a lateral opening 49 in the cover. The lateral opening 49 defines the extent of movement of the handle 150 and, thus, the extent of rotational movement of the actuating member 120 relative to the base 50. The extents 49a and 49b of the lateral opening 49 define the locked position and the unlocked position, respectively, of the actuating member 120. The cover 40 is fixed to the base 50 such that movement of the handle 150 relative to the cover effects movement of the actuating member 120 between the locked position and the unlocked position.

Once the locking device 30 is mounted within the cover 40, the elongated instrument 35 can be fed through the passage 56 of the base 50 while in the unlocked position. In the example embodiment illustrated in FIGS. 12-13, the elongated instrument 35 is rigidly coupled to a front handle 200 that is connected to a deployable stent (not shown) and releasably mounted to a rod 210 having a threaded outer surface 212. The stent may be deployable through the vasculature of a patient (not shown) to a desired position in the vessel requiring treatment. The rod 210 can be linear or steerable.

When it is desirable to advance the front handle 200 and, thus, the stent along the axis 36 in large increments in the direction indicated at arrow D, the handle 150 on the actuating member 120 is rotated in the direction A until the handle reaches the extent 49b of the opening 49 in the cover 40 to place the actuating member in the unlocked position. As described, for example, the locking surfaces 98 on the locking projections 96 on the rocker arms 80 move radially outward from the central axis 36 of the base 50 to space the locking surfaces from the major diameter of the threads 212 on the rod 210 and, thus, out of contact with the rod. The front handle 200 and, thus, the stent can then be advanced or retracted in large increments substantially freely along the axis 36 in the direction D relative to the locking device 30 by holding the front handle and moving the unlocked locking device 30 along the rod 210 relative to the front handle. Such axial movement may be desirable when the vasculature in which the stent is positioned is not tortuous or occluded.

To advance the front handle 200 and, thus, the stent along the axis 36 in fine increments in the direction D, the handle 150 on the actuating member 120 can be released or rotated in a direction opposite to the direction A until the handle reaches the extent 49a of the opening 49 in the cover 40 to place the actuating member in the locked position. Such movement may be desirable when the vasculature in which the stent is positioned is tortuous and/or occluded. By moving the actuating member 120 to the locked position, the locking surfaces 98 on the locking projections 96 on the rocker arms 80 move radially inward through the lateral openings 62 and toward the central axis 36 of the base 50 into engagement with the minor diameter of the threads 212 on the rod 210. The front handle 200 and, thus, the stent can then be advanced in the direction D only by rotating the locked locking device 30 in the direction indicated at E while holding the front handle. Since the locking surfaces 98 engage the space between the threads 212 of the rod 210, the pitch of the threads dictates how much rotational movement of the locking device 30 in the direction E is required to advance the front handle 200 in the axial direction D.

Since the handle 150 may be easily grasped or otherwise manipulated, the locking device 30 can be readily moved between the locked and unlocked positions in order to move the front handle 200 and thereby deploy and guide the stent through the vasculature in either substantial or fine axial increments. The present invention therefore allows a surgeon or other practitioner to make substantial axial positioning adjustments of the elongated instrument 35, such as the front handle 200 connected to the stent within the patient while the locking device 30 is in the unlocked position and then lock the locking device such that only fine axial positioning adjustments can be made in order to ensure accurate anatomical placement.

For instance, when the actuating member 120 is in the locked position, the front handle 200 can only move axially along the axis 36 relative to the base 50 by rotating the locking device 30. That is, in the locked position, the front handle cannot be pushed, pulled, slid or otherwise advanced in an axial direction without also rotating the locking device relative to the rod. Where the rod 210 has a threaded outer surface 212, axial movement of the front handle 200 generated by rotating the locking device 30 will depend on the configuration of the threads and, thus, the axial movement may be relatively small. Accordingly, the actuating member 120 may prevent the rod 210 and therefore the front handle 200 from substantial axial movement and allow only fine-tuned axial adjustment of the stent.

When the actuating member 120 rotates to the unlocked position, the locking surfaces 98 of the locking projections 96 become spaced from the threads 212 on the rod 210. As long as the handle 150 maintains the actuating member 120 in the unlocked position, the locking surfaces 98 of the rocker arms 80 remain spaced from the threads 212 on the rod 210 within the passage 56 of the body 50. The rod 210 is therefore capable of free axial movement relative to the base 50. In other words, no rotation of the locking device 30 is necessary in order to axially move the rod 210 and therefore the front handle 200 relative to the base 50. The rod 210 is thereby capable of moving substantially along the axis 36 to perform large axial adjustments to the position of the stent within the patient or otherwise.

When it is subsequently desired to limit the axial movement of the front handle 200, the handle 150 on the actuating member 120 is released or otherwise rotated in a direction opposite to the direction A, i.e., a clockwise direction as viewed in FIG. 11, to move the actuating member back to the first, locked position when the handle is rotated in the clockwise direction of released. The spring 152 connecting the actuating member 120 to the base 50 urges the actuating member towards the locked position. As the actuating member 120 returns to the locked position, the cam portions 140 on the actuating member disengages from the cam portions 100 of the rocker arms 80, causing the second ends 84 of the rocker arms to rotate back towards the outer surface 58 of the base 50. Likewise, the locking projections 96 move radially inward through the lateral openings 62 and beyond the inner surface 60 of the base 50 until the locking surfaces 98 engage between the threads 212 on the rod 210.

As the locking projections 96 move radially inward, the retaining potions 134 of the actuating member 120 rotate back into engagement with the retaining portions 110 of the rocker arms 80 to urge the locking projections 96 into the radially inward position engaging the rod 210. Once the actuating member 120 reaches the locked position, the rod 210 and therefore the front handle 200 is again prevented from axially moving relative to the base 50 without also rotating the locking device 30. The locked position of the actuating member 120 thereby limits the front handle 200 to fine, incremental axial movements caused by rotation of the locking device 30 relative to the rod 210. On the other hand, the unlocked position of the actuating member 120 allows the elongated instrument 35 and, thus, the front handle 200 secured thereto to move substantially in the axial direction relative to the base 50 without rotating the locking device 30.

What have been described above are examples and embodiments of the invention. It is, of course, not possible to describe every conceivable combination of components or methodologies for purposes of describing the invention, but one of ordinary skill in the art will recognize that many further combinations and permutations of the present invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A locking device comprising:
   a generally tubular base extending along an axis and having an outer surface and an inner surface defining a central passage therethrough, at least one lateral opening extends through a sidewall of the base from the outer surface through the inner surface;
   at least one rocker arm mounted to the base, the at least one rocker arm having a locking projection that extends radially inwardly to terminate at a locking surface and which is aligned with the at least one lateral opening of the base; and
   an actuating member rotatable about the axis and relative to the base between first and second positions, in the first position the actuating member engaging the at least one rocker arm to urge the locking projection radially inward through the lateral opening and beyond the inner surface of the tubular base, movement of the actuating member to the second position causes the locking projection to move radially outwardly through at least a portion of the lateral opening.

2. The locking device of claim 1, wherein the at least one rocker arm is pivotally mounted to the base.

3. The locking device of claim 1, wherein the at least one rocker arm further includes a cam portion extending outwardly relative to the outer surface of the tubular base, movement of the actuating member to the second position causing the actuating member to move the cam portion of the at least one rocker arm radially outwardly which causes movement of the locking projection outward through the at least a portion of the lateral opening.

4. The locking device of claim 3, wherein the actuating member includes at least one cam portion, movement of the actuating member to the second position causing the at least one cam portion of the actuating member to engage the at least one cam portion of the at least one rocker arm and move the at least one rocker arm radially outwardly.

5. The locking device of claim 1, wherein the actuating member includes a handle for rotating the actuating member between the first and second positions.

6. The locking device of claim 1, wherein the at least one rocker arm comprises two rocker arms and the at least one lateral opening comprises two lateral openings.

7. The locking device of claim 1 in combination with an elongated instrument, the combination comprising a rod extending through the central passage of the base, wherein when the actuating member is in the first position the locking surface engages the elongated instrument and when the actuating member is in the second position the locking surface does not engage the elongated instrument.

8. The locking device of claim 1, wherein a spring urges the locking projection radially outward through at least a portion of the lateral opening when the actuating member is in the second position.

9. The locking device of claim 1 in combination with an elongated instrument, the combination comprising a rod extending through the central passage of the base, wherein the elongated instrument is a threaded instrument, the locking surface engaging the minor diameter of the threaded instrument when the actuating member is in the first position, the locking surface being spaced radially outward from the major diameter of the threaded instrument when the actuating member is in the second position.

10. The locking device of claim 1, wherein the tubular base has a cylindrical inner surface.

11. The locking device of claim 1 in combination with an elongated instrument, the combination comprising:
   a rod of the elongated instrument extending through the central passage of the base, wherein when the actuating member is in the second position, the elongated instrument is substantially free to move axially relative to the base without rotating the locking device, when the actuating member is in the first position the elongated instrument is axially fixed relative to the base, except if the locking device is rotated.

12. A system for delivering an endoluminal prosthesis comprising:
   an elongated instrument; and
   a locking device slidably mounted about the elongated instrument, the locking device comprising:
      a tubular base extending along an axis and having an outer surface and an inner surface defining a central passage therethrough, at least one lateral opening extends through the tubular base from the outer surface through the inner surface;
      at least one rocker arm mounted to the base, the at least one rocker arm having a locking projection that extends inwardly through the lateral opening of the base to terminate at a locking surface which engages the elongated instrument; and
      an actuating member rotatable about the axis and relative to the base between first and second positions, in the first position the actuating member engaging the at least one rocker arm to urge the locking projection radially inward through the lateral opening and beyond the inner surface of the tubular base so as to prevent axial movement of the elongated instrument, movement of the actuating member to the second position causes the locking projection to move radially outward so as to allow substantially free axial movement of the elongated instrument.

13. The system of claim 12, wherein the elongated instrument comprises at least one of a stent, catheter, guidewire, and a cannula.

14. The system of claim 12, wherein the at least one rocker arm is pivotally mounted to the base.

15. The system of claim 12, wherein the at least one rocker arm further includes a cam portion extending outward of the outer surface of the tubular base, movement of the actuating member to the second position causing the actuating member to move the cam portion of the at least one rocker arm radially outward which causes movement of the locking projection out of engagement with the elongated instrument.

16. The system of claim 15, wherein the actuating member includes at least one cam portion, movement of the actuating member to the second position causing the at least one cam portion of the actuating member to engage the at least one cam portion of the at least one rocker arm and move the at least one rocker arm radially outwardly.

17. The system of claim 12, wherein the actuating member includes a handle for rotating the actuating member between the first and second positions.

18. The system of claim 12, wherein the at least one rocker arm comprises two rocker arms and the at least one lateral opening comprises two lateral openings.

19. The system of claim 12, wherein a spring biases the actuating member towards the first position.

20. The system of claim 12, wherein the elongated instrument is a threaded instrument, the locking surface engaging the minor diameter of the threaded instrument when the actuating member is in the first position, the locking surface being spaced radially outward from the major diameter of the threaded instrument when the actuating member is in the second position.

21. The system of claim 20, wherein when the actuating member is in the second position, the elongated instrument is axially movable relative to the base without rotating the locking device, the actuating member preventing substantial axial movement of the elongated instrument relative to the base when the actuating member is in the first position, wherein rotation of the locking device relative to the elongated instrument results in fine incremental movement of the threaded instrument relative to the base when the actuating member is in the first position.

22. The system of claim 12, wherein the tubular base has a cylindrical inner surface.

23. A method comprising:
   providing a locking device comprising:
      a tubular base extending along an axis having an outer surface and an inner surface defining a central passage, at least one lateral opening extends from the outer surface through the inner surface;
      at least one rocker arm mounted to the base, the at least one rocker arm having a locking projection that extends inwardly to terminate at a locking surface and which is aligned with the lateral opening of the base; and
      an actuating member rotatable about the axis and relative to the base between first and second positions, in the first position the actuating member engaging the at least one rocker arm to urge the locking projection radially inward through the lateral opening and beyond the inner surface of the tubular base, movement of the actuating member to the second position causes the locking projection to move radially outward through at least a portion of the lateral opening;
   inserting an elongated instrument through the central passage of the locking device;
   rotating the actuating member to the second position to allow axial movement of the elongated instrument without rotation of the locking device; and
   rotating the actuating member to the first position to allow axial movement of the elongated instrument only if the locking device is rotated.

* * * * *